United States Patent
WalkerPeach et al.

(10) Patent No.: US 6,395,470 B2
(45) Date of Patent: May 28, 2002

(54) METHOD FOR MONITORING NUCLEIC ACID ASSAYS USING SYNTHETIC INTERNAL CONTROLS WITH REVERSED NUCLEOTIDE SEQUENCES

(75) Inventors: Cindy R. WalkerPeach; Dwight B. Dubois, both of Austin, TX (US)

(73) Assignee: Cenetron Diagnostics, LLC, Austin, TX (US)

( * ) Notice: Subject to any disclaimer, the term of this patent is extended or adjusted under 35 U.S.C. 154(b) by 0 days.

(21) Appl. No.: 09/183,866

(22) Filed: Oct. 30, 1998

Related U.S. Application Data

(60) Provisional application No. 60/063,922, filed on Oct. 31, 1997.

(51) Int. Cl.$^7$ .............................. C12Q 1/70; C12Q 1/68; C12P 19/34
(52) U.S. Cl. .............................. 435/5; 435/6; 435/91.1; 435/91.2; 536/23.1; 536/24.1; 536/23.72; 536/24.3; 536/24.32; 536/24.33; 536/24.5
(58) Field of Search .............................. 435/5, 6, 91.2, 435/320.1, 91.1; 536/23.1, 24.1, 23.72, 24.3, 24.32, 24.33, 24.5

(56) References Cited

U.S. PATENT DOCUMENTS

| | | | |
|---|---|---|---|
| 4,683,202 A | | 7/1987 | Mullis |
| 5,059,538 A | * | 10/1991 | Nozaki et al. |
| 5,468,617 A | * | 11/1995 | Blaudin De The et al. .. 435/7.8 |
| 5,514,477 A | * | 5/1996 | Draper et al. |

OTHER PUBLICATIONS

Cone et al. Journal of Clinical Microbiology, Dec. 1992, vol. 30, No. 12, p. 3185–3189.*
Boom, et al., "Rapid and Simple Method for Purification of Nucleic Acids", Journal of Clinical Microbiology, 28(3): 495–503 (Mar. 1990).
Bzik, et al., "Nucleotide Sequence Specifying the Glycoprotein Gene, gB, of Herpes Simplex Virus Type 1", Virology, 133: 301–314 (1984).
Giesendorf, et al., "Molecular beacons: a new approach for semiautomated mutation analysis", Clinical Chemistry, 44 (3): 482–486 (1998).
Klevits, et al., "NASBA™ isothermal enzymatic in vitro nucleic acid amplification optimized for the diagnosis of NIH–1 infection", Journal of Virological Methods, 35: 273–286 (1991).
Pachl, et al., "Rapid and Precise Quantification of HIV–1 RNA in Plasma Using a Branched DNA Signal Amplification Assay", Journal of Acquired Immune Deficiency Syndromes and Human Retrovirology, 8: 446–454 (1995).
Smith, et al., "A Rapid, Sensitive Multiplexed Assay for Detection of Viral Nucleic Acids Using the FlowMetrix System", Clinical Chemistry, 44: 2054–2056(1998).
Stary, et al., "Performance of Transcription–Mediated Amplification and Ligase Chain Reaction Assays for Detection of Chlamydial Infection in Urogenital Samples Obtained by Invasive and Noninvasive Methods", Journal of Chemical Microbiology, 36(9), 2666–2670 (Sep. 1998).
Stuve, et al., "Structure and Expression of the Herpes Simplex Virus Type 2 Glycoprotein gB Gene", Journal of Virology, 61(2): 326–335 (Feb. 1987).
Sutton, et al., "Synthetic cryllA gene *Bacillus thuringiensis* improved for high expression in plants." Transgenic Research, 1: 228–236 (1992).
Tyagi & Kramer, "Molecular Beacons: Probes that Fluoresce upon Hybridization", Nature Biotechnology, 14: 303–308 (Mar. 1996).
Van heusden, et al., "Fluorescein–labeled Tyramide Strongly Enhances the Detection of Low Bromodeoxyuridine Incorporation Levels", The Journal of Histochemistry & Cytochemistry, 45(2): 315–319 (1997).
Antibodies, A Laboratory Manual, (Harlow and Lane, Eds.), Cold Spring Harbor Laboratory (1988). (title page only).
Current Protocols In Molecule Biology, vol. 2, Chapter 15 (1995).

* cited by examiner

*Primary Examiner*—Jeffrey Fredman
*Assistant Examiner*—Juliet Einsmann
(74) *Attorney, Agent, or Firm*—Knobbe, Martens, Olson and Bear, LLP

(57) ABSTRACT

The present invention relates to methods and compositions that provide a positive control to identify inhibition during a signal amplification reaction. The methods and compositions of the present invention are designed to run in the same tube or assay environment as the experimental or target sample and contain a copy of the target sequence in an inverted form.

13 Claims, 4 Drawing Sheets

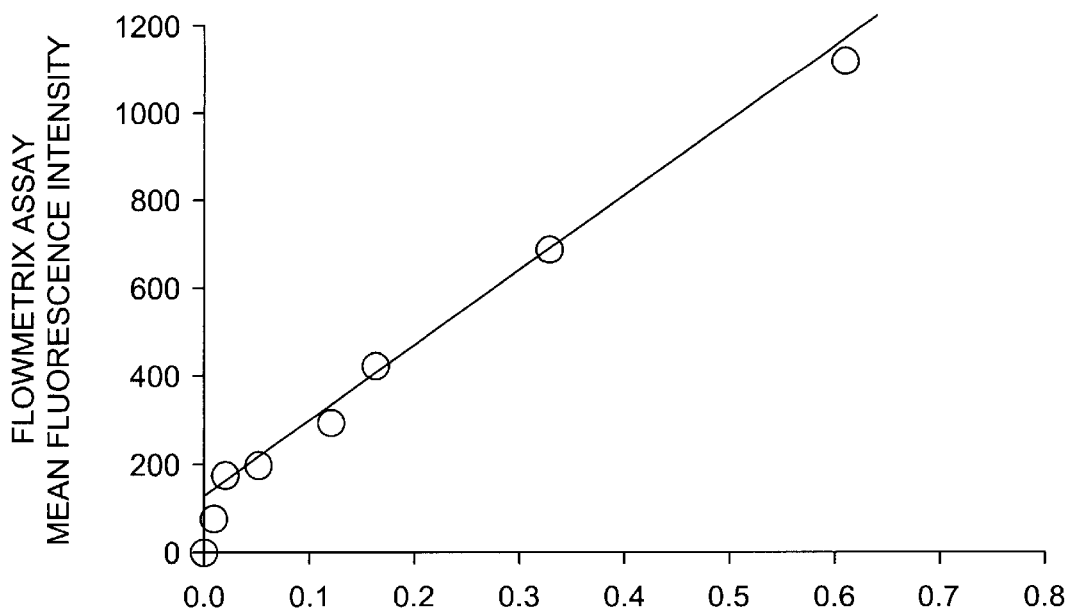
FIG. 4A  MICROTITER - BASED DETECTION OF ICC PCR PRODUCT ($OD_{450}$)
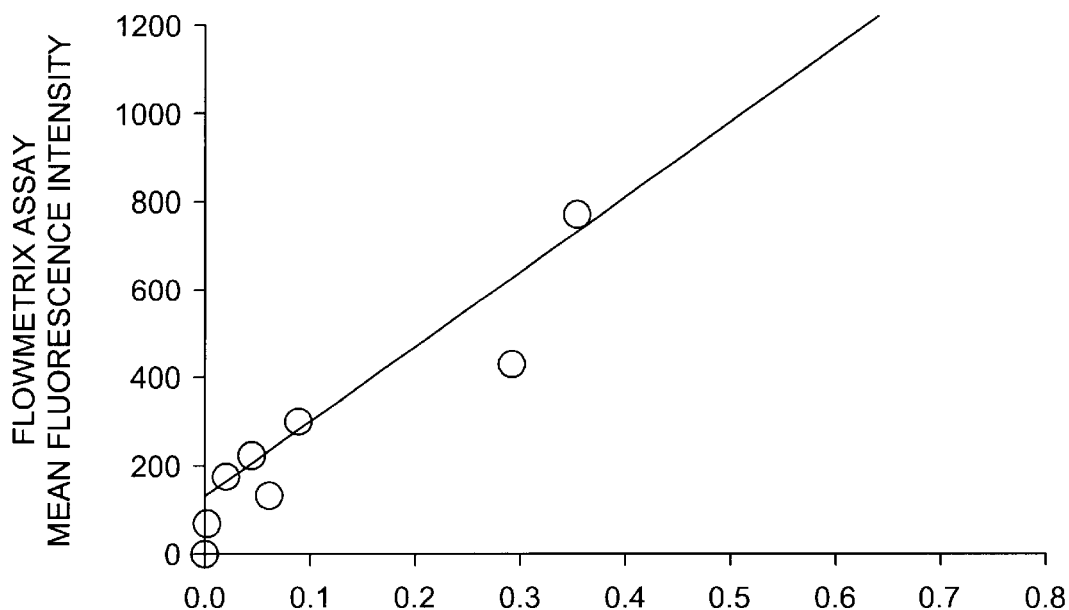
FIG. 4B  MICROTITER - BASED DETECTION OF HSV PCR PRODUCT ($OD_{450}$)

SEQUENCE LISTING

<160> NUMBER OF SEQ ID NOS: 8

<210> SEQ ID NO 1
<211> LENGTH: 148
<212> TYPE: DNA
<213> ORGANISM: Herpes simplex virus (HSV)

<400> SEQUENCE: 1
ttgaagcggt cggcggcgta gctggtgtgt tcggtgtgcg acccctcccg g tagccgtaa    60 aacggggaca tgtacacaaa gtcgccagtc gccaacacaa actcgtcgta c gggtacacc   120 gagcgcgcgt ccacctcctc gacgatgc                                      148

<210> SEQ ID NO 2
<211> LENGTH: 148
<212> TYPE: DNA
<213> ORGANISM: Artificial Sequence
<220> FEATURE:
<223> OTHER INFORMATION: Synthetic probe

<400> SEQUENCE: 2
ttgaagcggt cggcggcgta gctggtgtgt tcggtgtgcg acccctcccg c tgaaacaca    60 tgtacagggg caaaatgccg atggccagtc gccaacacaa actcgtcgta c gggtacacc   120 gagcgcgcgt ccacctcctc gacgatgc                                      148

<210> SEQ ID NO 3
<211> LENGTH: 20
<212> TYPE: DNA
<213> ORGANISM: Artificial Sequence
<220> FEATURE:
<223> OTHER INFORMATION: Synthetic probe

<400> SEQUENCE: 3
ttgaagcggt cggcggcgta                                                20

<210> SEQ ID NO 4
<211> LENGTH: 20
<212> TYPE: DNA
<213> ORGANISM: Artificial Sequence
<220> FEATURE:
<223> OTHER INFORMATION: Synthetic probe

<400> SEQUENCE: 4
gcatcgtcga ggaggtggac                                                20

<210> SEQ ID NO 5
<211> LENGTH: 39
<212> TYPE: DNA
<213> ORGANISM: Artificial Sequence
<220> FEATURE:
<223> OTHER INFORMATION: Synthetic probe

<400> SEQUENCE: 5
ggcgactttg tgtacatgtc cccgttttac ggctaccgg                           39

-continued

```
<210> SEQ ID NO 6
<211> LENGTH: 39
<212> TYPE: DNA
<213> ORGANISM: Artificial Sequence
<220> FEATURE:
<223> OTHER INFORMATION: Synthetic probe

<400> SEQUENCE: 6
ggccatcggc attttgcccc tgtacatgtg tttcagcgg                            39

<210> SEQ ID NO 7
<211> LENGTH: 49
<212> TYPE: DNA
<213> ORGANISM: Artificial Sequence
<220> FEATURE:
<223> OTHER INFORMATION: Synthetic probe

<400> SEQUENCE: 7
gcgagggcga ctttgtgtac atgtccccgt tttacggcta ccggctcgc                 49

<210> SEQ ID NO 8
<211> LENGTH: 49
<212> TYPE: DNA
<213> ORGANISM: Artificial Sequence
<220> FEATURE:
<223> OTHER INFORMATION: Synthetic probe

<400> SEQUENCE: 8
gcgagggcca tcggcatttt gcccctgtac atgtgtttca gcggctcgc                 49
```

METHOD FOR MONITORING NUCLEIC ACID ASSAYS USING SYNTHETIC INTERNAL CONTROLS WITH REVERSED NUCLEOTIDE SEQUENCES

RELATED APPLICATIONS

This application claims priority to U.S. Provisional Application 60/063,922, filed on Oct. 31, 1997.

BACKGROUND OF THE INVENTION

The present invention relates to the use of an internal positive control containing an inverse sequence to detect inhibition and to provide an internal quantitation standard in a nucleic acid assay.

Modern nucleic acid assay techniques allow researchers and clinicians to detect molecules of interest that are present in extremely low concentration. These assays use probes to specifically amplify by several orders of magnitude and detect the amount of the molecule of interest. However, when used diagnostically, falsely negative results arising from inhibition of the assay reaction dramatically reduce the predictive value of the assay. Thus there is a strong need for a method to control for inhibition of the assay reaction.

The Polymerase Chain Reaction (PCR) is an example of such an amplification technique for the detection of target molecules. With PCR it is possible to test blood samples for minute quantities of nucleic acid from pathogens, such as the human immunodeficiency virus (HIV). The technique can also be used to detect a variety of different infectious agents in a number of different clinical settings such as testing blood or donor organs for infection. Negative results may be unreliable given the susceptibility of these techniques to non-specific inhibition by a variety of compounds. Thus, there is a requirement for methods to differentiate true negative results from false negative results secondary to inhibition of the assay.

For the foregoing reasons, there is a need for an accurate reproducible positive control to detect inhibition in the PCR reaction. The method of detecting inhibition is further applicable to other signal amplification assays.

SUMMARY OF THE INVENTION

The present invention relates to compositions and methods that provide a positive control to identify inhibition during a signal amplification reaction. The methods and compositions of the present invention are designed to run in the same tube or assay environment as the experimental or target sample and contain a copy of the target sequence in an inverted form.

One embodiment of the present invention, provides for an internal control cassette for use in a polynucleotide detection assay in which a target sequence is detected. The target sequence has primer binding sites flanking an internal target sequence. The cassette comprises primer binding sites flanking an internal control sequence, wherein the internal control sequence comprises said internal target sequence in a reversed orientation.

In one aspect of this embodiment, the internal control cassette further comprises one or more primer binding sites adjacent to the internal control sequence. In another aspect, the internal control cassette further comprises the nucleic acid sequence of SEQ. ID. NO. 5. The internal control cassette may be a component of a plasmid.

Another embodiment of the present invention contemplates a method for detecting signal amplification inhibition in an assay comprising the steps of: co-amplifying a target sequence and an internal control cassette, wherein the internal control cassette comprises the target sequence in a reverse orientation. Assays contemplated for use with the present invention are selected from the group consisting of PCR, real-time PCR, branched DNA (bDNA)-based signal amplification assays, nucleic acid sequence based amplification assays (NASBA), and transcription mediated amplification (TMA).

The target sequences usable in the present invention include any nucleic acid sequence that may be assayed with techniques known in the art. In one aspect of this embodiment, the target sequence comprises DNA or RNA. In another aspect, the target sequence is a nucleic acid sequence from a virus selected from the group consisting of HSV, HIV, HCV, CMV, and HPV. In another aspect, the target sequence comprises the nucleic acid sequence of SEQ. ID. NO. 1.

Similarly, the internal control cassette sequences include any sequence that may be a target sequence. For example, an internal control cassette comprises the nucleic acid sequence of SEQ. ID. NO. 2.

The methods of the present invention further comprise the step of assaying products generated by the co-amplification described above. The present invention further contemplates an additional step of assaying products by a primer binding assay comprising the step of determining the extent of product binding to a capture probe specific for the internal control cassette product. In one aspect of this embodiment, the capture probe consists of the nucleic acid of SEQ ID NO. 6.

Another embodiment of the present invention contemplates a method for detecting signal amplification inhibition in an assay comprising the steps of contacting one or more hybridization probes with both a target sequence and an internal control cassette in the same medium, wherein the internal control cassette comprises the target sequence in a reverse orientation. For example, the assay of this embodiment is a molecular beacon assay. In another aspect, the internal control cassette comprises the nucleic acid sequence of SEQ. ID. NO. 2. In still another aspect, the hybridization probe comprises the nucleic acid sequence of SEQ. ID. NO. 8.

DESCRIPTION OF THE DRAWINGS

FIG. 4 graphically depicts a comparison of samples assayed using the Flowmetrix assay of Example 5 against the microtiter based detection system of Example 3.

DETAILED DESCRIPTION OF THE INVENTION

Figure 1:
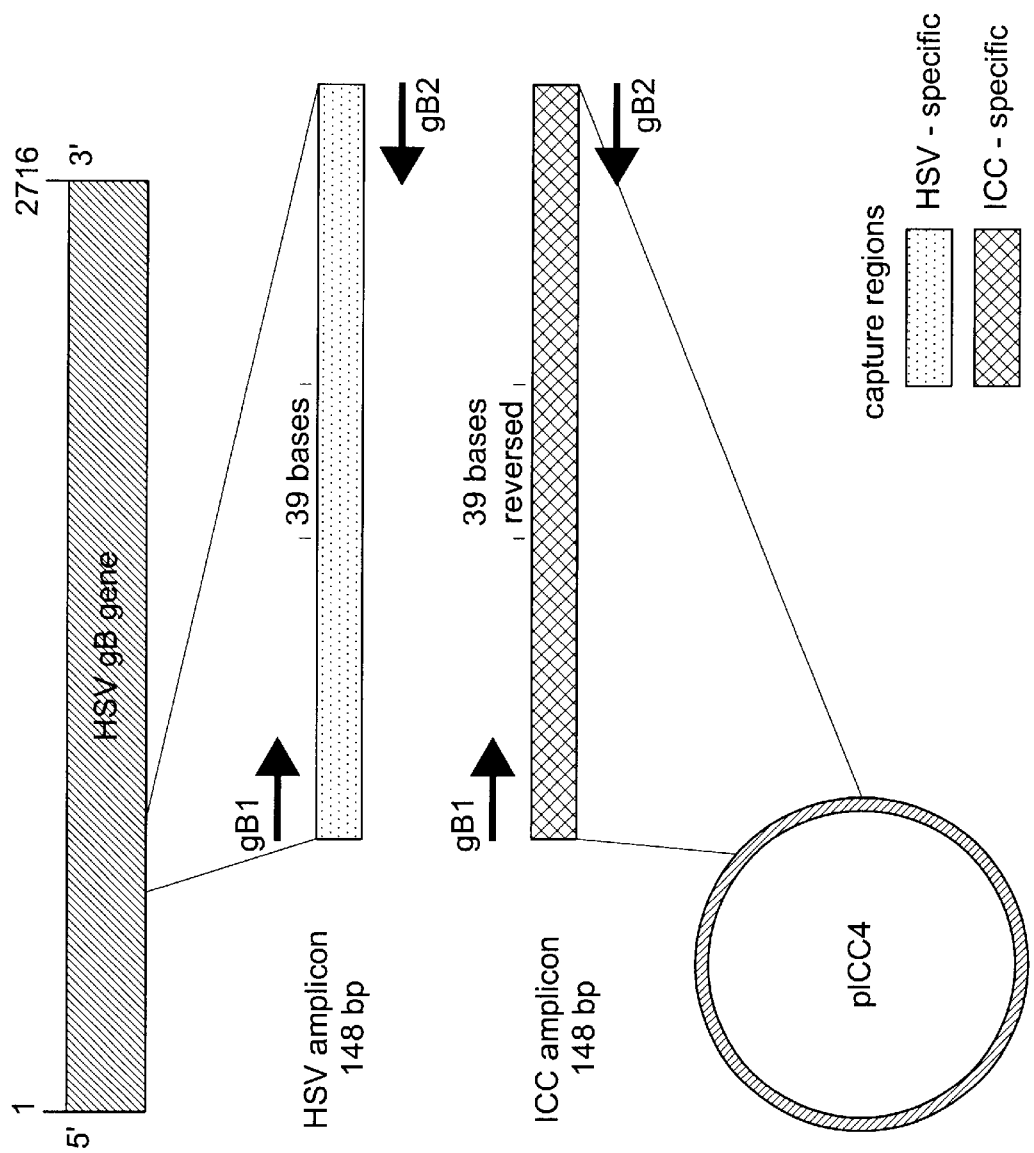
FIG. 1 graphically depicts the HSV gB target and ICC sequences.

The present invention relates to methods and compositions that provide a positive control to identify inhibition during a signal amplification reaction. The methods and compositions of the present invention are designed to run in the same tube or assay environment as the experimental or target sample and contain a copy of the target sequence in an inverted form.

The methods and compositions of the present invention offers a number of advantages over other methods of controlling the variables of signal amplification assays. One benefit of the present invention's design relates to the possible presence of inhibitors in the reaction mix. The methods described herein provide the means to control for inhibition in the experimental reaction.

Traditionally, a signal amplification assay is conducted with an experimental sample and positive and negative controls run in separate tubes, wells, or assay environments. The goal of these assays is to examine the experimental sample for the presence or absence of a target sequence. The positive control sample provides a check to insure the functionality of the assay's reagents. The negative control sample provides a means to determine the background signal.

After the assay is run and the results are generated, one of skill in the art will examine the experimental well for a signal. The presence or absence of a signal indicates the presence or absence of the target molecule. In the positive control sample, the presence or absence of a signal indicates whether or not the assay's reagents are functional. Thus, if there is no signal in the experimental well but a signal in the control well, one of skill in the art may conclude that there is no target sequence in the experimental well, since the result from the control well indicates that the assay's reagents are functional.

This conclusion will be accurate if the reason for the absence of signal from the experimental well is that there is no target sequence contained therein. If, on the other hand, there are contaminants in the experimental sample that result in the inhibition of the signal amplification reaction, then no signal will be produced even though a target sequence is present in the experiment sample. The positive control sample will produce a signal, indicating that the reagents used in the assay are functional. Under these conditions, one of ordinary skill in the art could incorrectly interpret the result from the signal amplification assay as a negative result.

The methods and compositions of the present invention are superior to traditional standards because, by combining experimental and control fragments into one environment, one is capable of detecting the presence of an inhibitor in the reaction mixture. This capability is especially important in the clinical setting. In a conventional prior art positive control system, when a blood sample is tested for the presence of a particular target molecule, such as a viral nucleic acids, the experimental and control reactions are tested separately. A positive control sample is run along side the experimental sample to insure that the reagents used in the reaction are functioning properly. For example, the experimental tube could contain a sample of blood, the amplification primers, and the other reagents. In a separate tube a positive control reaction is set up using a known target sequence, appropriate primers, and a sample of the same reagents used in the experimental tube. After the PCR reaction is complete, the results are examined.

If a positive control for inhibition is included in the experimental tube, (i.e., an internal positive control) then the clinician can more confidently determine whether the target molecule was actually present, or whether the results obtained were merely a false negative. If no signal is obtained from the assay's experimental well, then there was inhibition of the assay reaction. If a signal is obtained from only the internal positive control but not from the target molecule, then it is reasonable to conclude that there was no target molecule present in the sample. A benefit of the present invention is that it permits an investigator to differentiate a true negative result from a false negative caused by inhibition in the experimental reaction sample.

The present invention contemplates utility for use as an internal inhibition control in a variety of signal amplification assays. Examples of signal amplification assays include: the polymerase chain reaction (PCR), variations of PCR, including reverse transcriptase PCR, real-time PCR, branched DNA (bDNA) assays, nucleic acid sequence based amplification assays (NASBA), transcription mediated amplification (TMA), cytoflowmetric assays, molecular beacon assays, hybridization reactions, and detection assays.

The internal control cassette (ICC) may consist of any target sequence that may be amplified by PCR or other nucleotide amplification techniques. Sequences that are present in clinically important disease states are particularly relevant to the present invention. Examples provided for illustrative purposes include sequences from viruses such as human immunodeficiency virus (HIV), herpes simplex virus (HSV), hepatitis C virus (HCV), human papilloma virus (HPV), and cytomegalovirus (CMV). Examples of particular genes that may be used as target sequences include the HSV gB gene and the HIV gp24 and gag genes.

As discussed above, the present invention provides a method to control for inhibition of signal development in an experimental well within a signal amplification assay. The ICC of the present invention provides the template from which the internal control signal is generated.

The ICC constructs of the present invention may be comprised of a number of elements used to generate the control signal. The ICC advantageously comprises a target sequence with an internal segment in an inverted orientation, with respect to the target sequence as it appears in nature, and one or more primer binding sites. The segment of sequence inverted in the ICC preferably lies immediately adjacent to or is flanked by the amplification primer binding site or sites that are used to amplify the experimental target sequence.

The entire construct may be a plasmid or some other replicating construct. Alternatively, the ICC may be a linear fragment of nucleic acid or polymerized amino acids. When the ICC is a plasmid, the plasmid may be of bacterial origins.

A plasmid used to construct the ICC can advantageously contain all of the necessary components found in any bacterial plasmid used in the field of molecular biology. For example, an origin of replication which would permit it to replicate within host bacteria may be included. Also, a suitable plasmid may contain a drug resistance marker, such as the ampicillin or tetracycline resistant markers. Further, a suitable plasmid may contain a multiple cloning site to facilitate the cloning of the target sequence to be used in the ICC. Other necessary or useful plasmid components may also be included in a plasmid used to construct an ICC, according to the judgment exercised by one of ordinary skilled in the art.

The present invention also contemplates the use of an internal control for RNA signal amplification assays. In a preferred embodiment, a control plasmid for use in an RNA signal amplification assay is prepared as described above. In another preferred embodiment, an inducible promoter (such as lac) and a sequence such as a poly(A) tail are cloned at the 5' and 3' ends of the inverted target sequence (respectively) in the multiple cloning site of the internal control plasmid. Using this plasmid it is possible to produce RNA molecules (via in vitro transcription) which contain the inverted capture sequence of a particular target gene and as such would provide a suitable reagent with which to control for inhibition of a RNA based amplification reaction.

Other methods of controlling for inhibition often use random sequences of nucleotides as the target for the control reaction. Nevertheless, use of random sequences does not accurately reflect the biochemical limitations that come into play during the amplification of a particular target sequence. These differences, for example, in differences in nucleotide frequency or differences in the overall chemical nature between a target sequence and a control sequence may have a significant impact of the final yield.

The present method differs from those methods of the prior art in that it uses the same sequence as the target in the internal control construct, although an internal segment is inverted. By using an inverted sequence of a proposed target, as opposed to a randomly generated control sequence, the present invention creates a control sequence that shares many of the same biochemical characteristics of the target sequence (e.g., reaction kinetics, temperature of melting ($T_M$), and nucleotide composition).

One shared feature is that the same primers may be used to amplify both the control and target sequences. When the same primer pair is used for both sequences, the hybridization or primer annealing conditions for both the experimental and ICC control sequences are the same. Thus, using the same primers and primer binding sites for both sequences eliminates another variable which might effect the signal produced from the control and target sequences.

The choice of primers, their length and coding sequence are a preference of one of ordinary skill in the art. For example, when the primers are for use in a PCR reaction, the primers may be about 5 to 50 nucleotides long. Alternatively, each primer may be about 10 to 40 nucleotides long. In yet another alternative, each primer may be 15 to 35 nucleotides in length.

Using the inverted control sequence of the present invention also provides a number of quantitative similarities between the sequences that improves the significance of the inhibition control. This quantitative sequence similarity between target and control ICC sequences provides a number of advantages over conventional methods. For example, since the amplified sequences of the target and control plasmids are of the same length and composed of the same nucleotide bases, the reaction parameters for the two plasmids are identical. Reaction parameters such as the $T_M$, the length of the sequence amplified, primer annealing or hybridization and primer usage are all substantially the same for the experimental and control sequences of the present invention. Given the similarity in reaction parameters between the two sequences, the yield of the co-amplification reactions should also be similar. Thus the inverted sequence of the control plasmid provides an extremely valid method for investigators to monitor for inhibition during signal amplification reactions.

The present invention allows an investigator to control for inhibition of a sequence amplification reaction with a control sequence that has the same $T_M$ as the target sample. The $T_M$ of interacting nucleic acid strands is determined by their sequence. Here, the control and target sequences both have the same composition of nucleotide base pairs arranged in the same sequence, albeit inverted. Therefore, the internal control and target sequences have the same $T_M$.

The importance of using a control sequence that binds assay primers with the same $T_M$ as the target sample becomes clear when the steps of the assay method are examined. For example, during PCR subsequent rounds of denaturation, annealing and polymerization are used to create a PCR product. During the denaturation step, as the temperature rises, the forces which hold the target strands together will be insufficient to keep the molecule double stranded. When the template becomes single stranded, it is available to bind the primers and the enzyme of the PCR reaction.

Sequences that have higher $T_M$s, may require more heat to serve as efficient templates in the PCR reaction. This comes from the fact that G, C, A, and T, each bind to each other with either 2 or 3 hydrogen bonds. Thus, one utilizes a less accurate control when the positive control sequence and its corresponding primer or probe has a different Tm than that of the experimental sample and its corresponding primer or probe. Accordingly, one should avoid merely random sequences.

Another important feature of the present invention is the length and composition of the control sequence. The length and composition of the sequence amplified may effect the signal obtained from the assay. During polymerization, the action of the synthesizing enzyme traveling down the template strand is known as processivity. The processivity of the enzyme may decrease as the length of the target sequence increases. So, the longer the target sequences, the more likely that it is that the PCR enzyme will fall off the template before completing the synthesis of the replicated strand. Premature termination of polymerization results in a product that differs in length from the target sequence and that difference could be misread as a negative result.

The positive control of the present invention eliminates this problem. Since the amplified region of the positive control plasmid is the same length as the target sequence, the rate of premature termination should be the same for both sequences. As a result, if there are apparent qualities of the target sequence which cause the PCR enzyme to fall off, those same characteristics should be present in the inverted control sequence and the PCR enzyme should fall off that sequence as well.

Particular embodiments of the invention are discussed in detail below. The following examples are for illustrative purposes only and should not be interpreted as limitations of the claimed invention. There are a variety of alternative techniques and procedures available to those of skill in the art that would similarly permit one to successfully perform the intended invention.

EXAMPLE 1

Internal inhibition control plasmid construction

Construction of an internal control cassette (ICC) involved creating a DNA fragment containing a portion of the HSV (herpes simplex virus) gB gene (148 base pairs, nucleotide numbers 797–945), with the central 39 base pairs (nucleotide numbers 859–898) in the reverse orientation. (See FIG. 1). The gB gene was discussed in Stuve, et al., "Structure and expression of the herpes simplex virus type 2 glycoprotein gB gene." J. Virol., 61(2):326–335 (1987) and Bzik, et al., "Nucleotide sequence specifying the glycoprotein gene, gB of herpes simplex virus type 1." Virology 133:301–314 (1984)(herein incorporated by reference). See also, Sutton, et al., Transgenic Research 1:228–236. (1992). The total length of the ICC fragment was 160 base pairs which includes the 148 base pair region and a unique restriction endonuclease site on each terminus of the fragment (5'=EcoRI, 3'=XhoI) for cloning purposes.

De novo construction of the HSV-ICC fragment was performed using PAGE purified oligodeoxynucleotides, a ligase chain reaction developed for synthetic gene construction (modified from Sutton, et al., 1992) and a thermostable ligase (Ampligase™, Epicentre Technologies, Madison, Wisc.). After construction and cloning, sequence verification was performed by dye-terminator sequence chemistry (ABI 337).

A claiming plasmid pBluescript KS (Stratagene, San Diego, Calif.) was chosen to carry the internal control sequence. Any plasmid capable of replication in bacteria and suitable for molecular biological manipulation may serve. The multiple cloning region of the control plasmid was then cut with restriction endonucleases which correspond to the sites on the de novo constructed DNA fragment (which contained the central reversed capture region). The restriction enzyme digestion created a linear plasmid that accepted the exogenous nucleic acid sample that was the internal control sequence. The digested control plasmid was then isolated from the digestion reaction using standard techniques known to those with ordinary skill in the art. Those techniques include but are not limited to the use of glass beads, various column matrices, gel isolation, etc.

The purified cleaved plasmid was then mixed with the purified fragment and the DNA molecules were ligated together using standard techniques known in the art. A DNA ligase was used to close the phosphate backbone of the newly formed internal control plasmid.

EXAMPLE 2

Internal inhibition control for the Polymerase Chain Reaction (PCR)

Example 2 below discusses the inhibition detection technology of the present invention for use with the polymerase chain reaction. This method recites the use of a target nucleotide sequence and a pair of primers that are complementary to that sequence. The method discussed below also comprises the use of an internal control plasmid in which the control sequence is the inverted nucleotide sequence of the target sequence. The primers used in the reaction are complementary to both the target sequence and to the internal control construct. PCR was then performed on the mixture.

In the PCR reaction, a target sequence is amplified by several orders of magnitude using a template, a pair of primers and a DNA polymerase enzyme. Typically, a control reaction is run side-by-side with the experimental reaction to determine the functionality of the reagents. PCR provides a powerful tool for detecting small quantities of a target nucleic acid sequence in solution. Nevertheless, the use of a traditional positive control does not provide an investigator information as to whether or not the polymerization reactions in the experimental tube has been inhibited. The protocol described below includes the internal inhibition control of the present invention that permits the investigator to detect the presence of signal amplification inhibition.

Once the templates, primers and reaction reagents are collected and mixed, sufficient heat is applied to the sample to denature the double stranded complex. Polymerization primers are then permitted to anneal to the denatured template. The primer-template complex of the PCR reaction is then bound by the DNA polymerase enzyme. The Taq polymerase is an example of a PCR suitable DNA polymerase. The DNA polymerase then proceeds to synthesize a polynucleotide that is complementary to the target strand. After a given period of time the enzyme is disassociated from the template. The cycle is then repeated. Repetition of this method permits the amplification of a given sequence as many as $4 \times 10^6$ times in twenty-five cycles of the PCR reaction. The PCR reaction is described in further detail in Mullis (1987) U.S. Pat. No. 4,683,202, herein incorporated by reference.

A polymerase chain reaction is performed using the protocol described below. This protocol is based on Current Protocols in Molecule Biology Volume 2, Chapter 15.1 (1995), which is incorporated herein by reference. A PCR amplification buffer concentrated 10 fold is prepared. The 10× PCR amplification buffer contains: 500 mM KCl, 100 mM Tris-HCl, pH 9.0 (at 25° C.); 0.1% Triton X-100. The four nucleotide triphosphates (dNTPs) are mixed for ease of application. For example, the 2.5 mM 4dNTP mix is made by combining equal volumes of each dNTPs at a concentration of 10 mM. These reagents are all commercially available. Two primers, one in the forward and one in the reverse orientation are designed based on standard principles known in the art. These primers are diluted to a concentration of 20–50 pmol/$\mu$l in $H_2O$.

Template DNA is selected using standard parameters well known in the art. In this Example, the template consisted of 1 pg of viral genomic DNA/10 $\mu$l. An inhibition control ICC is used in combination with the 1 pg of genomic DNA a mixture containing approximately 500 copies, bringing the final volume to 10 $\mu$l.

An enzyme suitable for PCR, such as Taq DNA polymerase, is used at a starting concentration of 5 U/$\mu$l. Magnesium chloride has been shown to effect PCR reactions, so three concentrations of the salt were prepared: (L)15 mM, (M)30 mM and (H)45 mM $MgCl_2$. Sterile mineral oil was used to seal the reaction.

The PCR reactions are performed with the following volumes of reagents (final concentrations): 10 $\mu$l of the 10× PCR amplification buffer, 1 $\mu$l Primer 1 (0.5 $\mu$M), 1 $\mu$l Primer 2 (0.5 $\mu$M), 10 $\mu$l of Template DNA, 2 $\mu$l of 10 mM 4dNTP mix, 0.5 $\mu$l of Taq polymerase (2.5 U), and $H_2O$ to 90 $\mu$l. The protocol requires that 90 $\mu$l each of the master mix be placed into three 0.2 ml tubes labeled L, M, and H. To each tube was added 10 $\mu$l of each corresponding concentration of $MgCl_2$ so that the final concentrations are 1.5, 3.0 and 4.5 mM, respectively.

A commercially available thermocycler is used to perform the PCR reaction cycling of temperatures. The following steps listed compose one PCR cycle. The reaction tubes are denatured for 1 minute at 94° C. Next, the primers are annealed to the template between 55 and 60° C. depending on the $T_M$ of the primers.

The primers are extended on the template at 72° C. for 1 to 3 minutes depending on the length of the target sequence. The longer the sequence to be amplified, the longer the extension time. Once the cycle is complete, the thermocycler returns to the denature step. The reaction cycled for 25 to 30 times.

The results of the PCR reaction are assessed after the reaction is complete. If the positive control shows PCR product by detection methods well known in the art, the investigator will know that the reagents used in the reaction are functional. If an experimental signal is present, then the investigator knows that the sample contains the molecule of interest. If, however, there is no experimental signal, then the investigator needs to evaluate the signal from the ICC. If a signal is present from the ICC but not from the experimental sample, then the results are negative and the investigator may conclude that there is no detectable target sequence in the experimental sample. Alternatively, if there is no signal from either the experimental sample or the ICC, then the investigator may conclude that some inhibitory factor is present in the experimental sample and that the negative results may or may not indicate the presence of the target sequence in the experimental sample.

EXAMPLE 3

Detection of Herpes Simplex Virus Type 1 (HSV-1) and Type 2 (HSV-2) in Cerebral

Spinal Fluid by Qualitative Polymerase Chain Reaction

This Example details procedures for using a PCR-based assay for detecting HSV-1 and HSV-2 DNA in cerebral spinal fluid (CSF). Detection of these viruses is an essential step in determining whether patients are chronically infected with these specific viruses.

The CSF used in this assay was obtained by spinal tap according to techniques well known in the art. Upon collection of the CSF, the sample was refrigerated at 1–4° C. or frozen at −20° C. if storage lasted more than one week.

Samples obtained for amplification included CSF from two patients Patient#21002 and Patient #28350, normal CSF (negative control) and normal CSF spiked with cultured HSV as a positive control. These samples were prepared and co-amplified with an ICC to assay for the presence of HSV.

As described in the Example above, a master mix of reagents was assembled for use in the PCR assay.

A 250 µl sample of CSF was placed into a 2 ml microcentrifuge tube and subjected to centrifugation at 1350 revolutions per minute (RPM) (1730 g) for 5 minutes. Two 100 µl samples of CSF were removed from the tube and pipetted into two separate 1.5 ml conical microcentrifuge tubes. The next step was to add 500 µl phosphate buffered saline (PBS) into all experimental and control tubes. This solution was vortexed well to mix the CSF and PBS.

Control samples were prepared in 1.5 ml conical microcentrifuge tubes to monitor the PCR reaction. The positive control consisted of 100 µL of 1 µl stock HSV in 10 ml of deionized water (ddH$_2$O). The negative control consisted of 100 µl of ddH$_2$O. The marked patient samples and control tubes were centrifuged for 1 hour at 21,000 RPM (39,444 g) at 4° C. At this point there were two samples per patient and and two negative and positive controls.

Supernatant was removed from the spun samples, being careful not to aspirate any precipitated matter. Approximately 10 µl of supernatant remained in the tube after aspiration. Next 10 µl of 0.025% BSA was added to the Lysis Buffer, which contained 0.4% (weight to volume) tergitol type NP-40; 1.25 mM DTT; and 4,000 copies of ICC/ml. In turn, 100 µl of this lysing reagent was added to each tube. The tubes were left to incubate at room temperature for 10 minutes. After the incubation, 50 µl of the solution from each sample was placed into a separate PCR tube.

To that tube was added 50 µl of the master mix. The master mix contained the following reagents: PCR reaction buffer, 25 mM MgCl$_2$, 10 mM dNTP, 20 mM dUTP, 100 µM PCR Primer gB$_1$ (SEQ ID NO. 3), 100 µM PCR Primer gB$_2$ (SEQ ID NO. 4), 1 Unit/µl of HK-UNG (Thermolabile Uracil N-Glycosylase; Epicentre Technologies, Madison, Wisc.), 5 Units/µl Taq, and ddH$_2$O. The primers were biotinylated to facilitate product detection following the amplification reaction. After the addition of the master mix, the tubes were placed into a thermocycler and amplified. Table 1 below describes the steps of the program.

TABLE 1

| Thermocycler Program | |
|---|---|
| #CYCLES | TIME AND TEMPERATURE |
| 1 | 30 minutes at 37° C. |
| 1 | 3 minute at 95° C. |
| 5 | 95° C. for 45 seconds, 64° C. for 45 seconds, 72° C. for 45 seconds |
| 30 | 95° C. for 15 seconds, 64° C. for 15 seconds, 72° C. for 15 seconds |

After the completion of the amplification, the samples were removed from the thermocycler. Denature Solution consisting of 1.6% NaOH, 1 mM EDTA and amaranth dye (Roche)(25 µl) was added to each sample followed by mixing. These samples were analyzed for the presence of replicated materials and are discussed below.

EXAMPLE 3

Assay for Determining the Presence of Replication Products

A microtiter plate based assay was used to determine the presence or absence of amplification products. This assay utilized a DNA capture probe to assay the products of the PCR reaction described in Example 2. This microtiter assay may also be used to assay amplification products produced by amplification reactions other than PCR.

Capture probes, such as the HSV gB probe (SEQ. ID. NO. 5) or the ICC probe (SEQ. ID. NO. 6) were coupled to an amino group at the 5' ends of the capture probes via a six carbon linker. The probes were synthesized with the linker already attached using standard phosphoamidite chemistry, which is well known in the art. The HSV gB probe was an antisense probe with a sequence that corresponded to nucleotide positions 1803 to 1841 of the gB gene of both HSV-1 and HSV-2. The ICC capture probe was specific for the ICC PCR product. (See FIG. 1).

The labeled capture probes were applied to the wells of high binding flat bottom 1×8 strip well microtiter plates. (Coming Costar). To the plate was added 100 µl/well of amine modified capture probe in probe binding buffer (50 mM Na2PO4, pH 8.5, 1 mM EDTA) at a concentration of 25 pmol/well or greater. The plate was then incubated overnight at 4° C. The unbound probe was removed from the plate by washing the plate three times with PBS. Next, the plate was blocked by adding 200 µl of 3% BSA in the probe binding buffer. This was incubated for 30 minutes at 37° C. at which time the solution was decanted.

The amplified specimen samples, 50 µl per reaction tube, were the transferred into each well of the prepared plate and mixed 5 times. The plate incubated for 1 hour at 37° C. Following the incubation the plate was washed five times using 1× wash solution with an automated tray washer. The 1× wash solution consisted of 10 mM phoshate buffer (pH 7.2), 150 mM NaCl, 1 mM EDTA, 0.5% PROCLIN 300. To the washed plates was added 100 µl/well of conjugate solution. The conjugate solution consisted of: 25 mM Tris- HCl, pH 7.5, 500 mM NaCl, 1.25 µg/ml Streptavidin-horseradish peroxidase, and 0.1% (v/v) Tween-20. The plate was incubated for 15 minutes at 37° C. following addition of the conjugate solution. Following this incubation, the plate was again washed 5 times with 1× wash solution using an automated plate washer. To the washed plates was added 100 µl of substrate solution that consisted of 51.4 mM $Na_2HPO_4$, 24.3 mM Citric Acid, 1 mg/ml 3,3', 5,5'-Tetramethylbenzidine Dihydrochloride, and 40% (v/v) N.N-Dimethylformamide. Following addition of the substrate, the plate was covered to exclude light, and was incubated at room temperature for 5 minutes. After the incubation period, 100 µl of stop solution was added to each well. The plate was then read at an optical density of 450 nm and the results are shown in FIG. 2.

Figure 2:
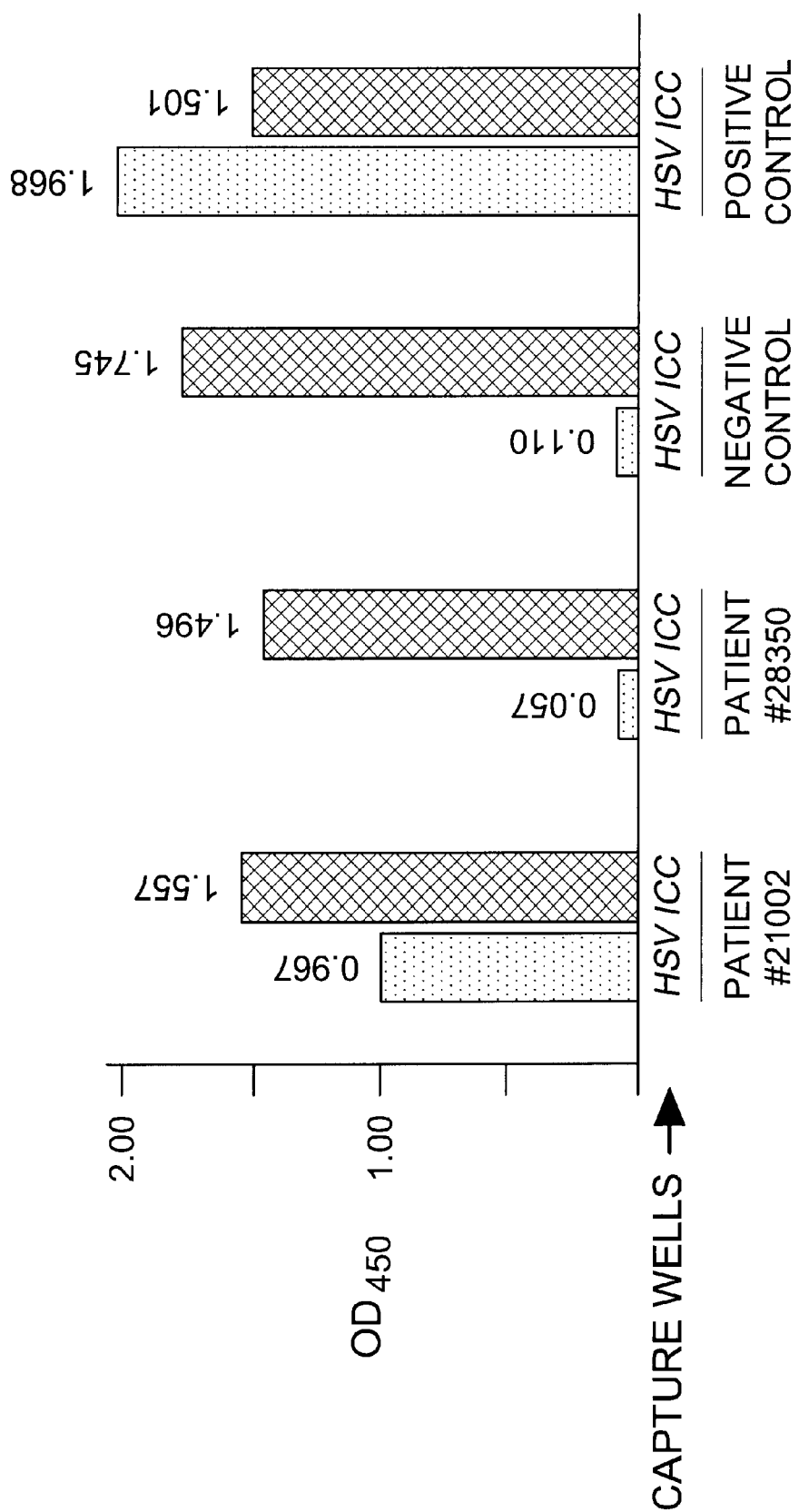
FIG. 2 graphically depicts the amount of product produced in a PCR reaction. The shaded bars represent HSV-related product and the filled bars represent ICC-related product. The magnitude of the bar are the optical density of the samples read at 450 nm.

FIG. 2 shows the enzymatic activity detected from the samples prepared in Example 2. Patient #21002 is clearly positive for HSV while Patient#28350 is negative for HSV viral DNA. Additionally, the controls indicate that there were no inhibitory substances in the PCR reaction mix, so that the absence of an HSV signal may be confidently interpreted as the lack of HSV target sequence, rather than a false negative. This conclusion was supported by the strong signal produced by the ICC sequence in all of the samples tested.

EXAMPLE 4

Specificity of HSV and ICC Capture Probes

To address the possibility of cross reactivity between the HSV and ICC capture probes, genomic HSV DNA or purified ICC plasmid DNA was amplified along with a water based negative control using the biotinylated primers (SEQ. ID. NOS. 3 and 4) and reaction conditions discussed above in Example 2. At the conclusion of the PCR reaction, the samples containing the HSV amplicon (SEQ. ID. NO. 1) or the ICC amplicon (SEQ. ID. NO. 2) or no amnplicon (negative control) were individually alkali denatured (denaturing reagent) and aliquoted into microtiter plate wells and allowed to hybridize in neutralizing buffer. The assay was performed as described in Example 3.

The wells contained a solid-phase bound oligonucleotide sequence probe specific for either HSV (SEQ. ID. NO. 5) or the ICC amplicon (SEQ. ID. NO. 6). After the hybridization and washing steps of the assay protocol, an avidin-horseradish peroxidase (AV-HRP) reagent was added to the wells. The AV-HRP bound to the biotin-labeled PCR products that were in turn bound to the plate via their interaction with the capture probes. The bound AV-HRP conjugate present in each well was detected by a reaction with peroxide and tetramethylbenzidine to form a colored product. The optical density ($OD_{450}$) was determined spectrophotometrically. The results of this experiment are shown in FIG. 3.

Figure 3:
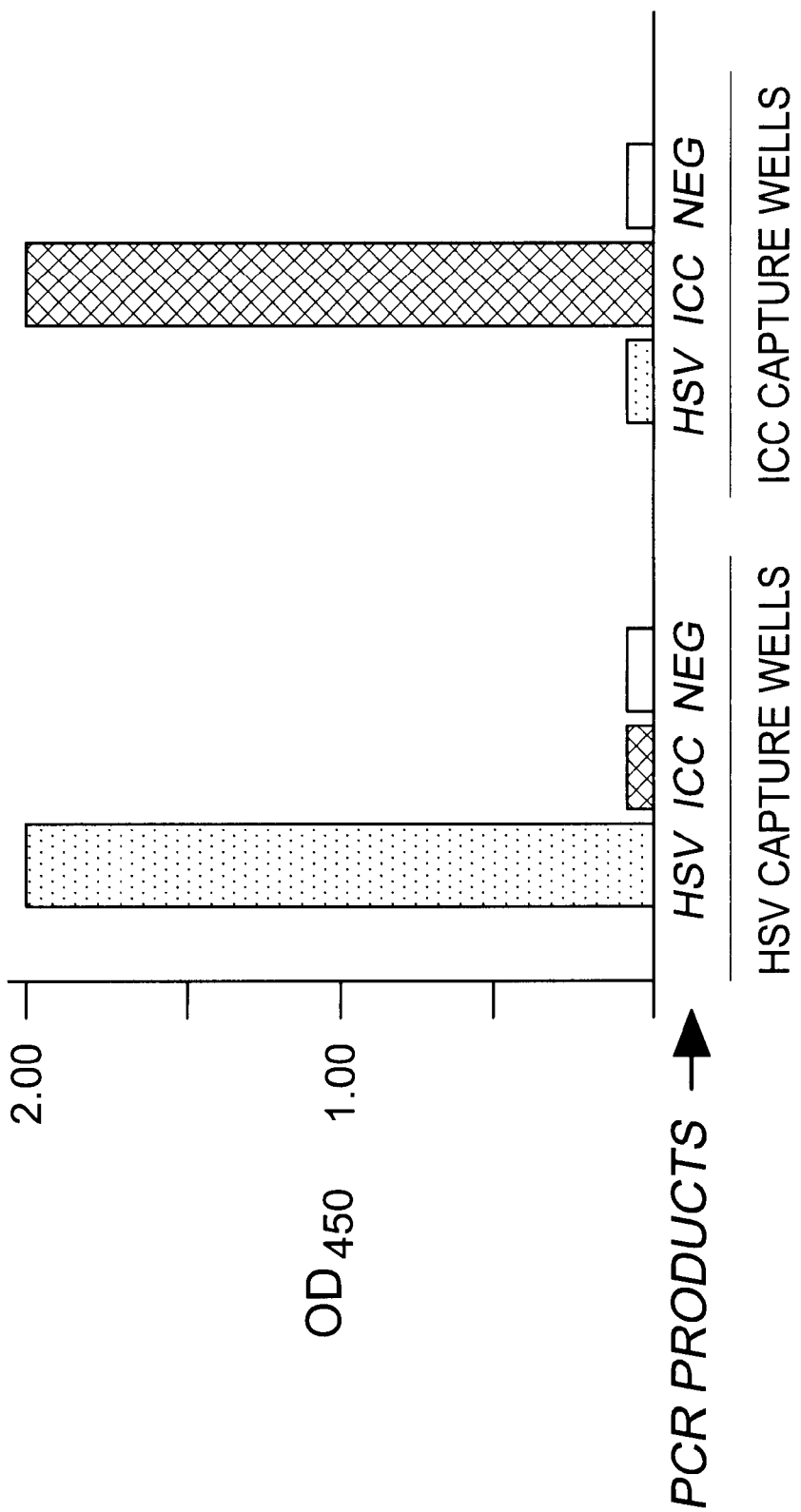
FIG. 3 graphically depicts the amount of product produced in a PCR reaction and the specificity of the signals produced therein. The shaded bars represent HSV-related product and the filled bars represent ICC-related product. The magnitude of the bar are the optical density of the samples read at 450 nm.

The data in FIG. 3 show that the HSV PCR product bound specifically to the HSV capture probe containing wells, while the ICC product only bound to the ICC capture probe containing wells. These results show the specificity of the various capture probes for their target sequences.

Alternative Probe Detection Assays

One aspect of the present invention contemplates a probe specific for the internal inhibition control plasmid bound to a fluorescently labeled microsphere. For example, probes specific for target sequence and ICC PCR products, respectively, are used to assay for the presence of herpes simplex virus (HSV) DNA in a sample using the FlowMetrix™ cytometric microsphere technology (Luminex Corp., DeSoto, Tex.).

EXAMPLE 5

Detection of PCR Products Using Flow Cytometric Microsphere Technology

In this Example, two sequence specific oligonucleotide probes, one for the HSV gB gene PCR product (SEQ ID NO 5) and one for the ICC product (SEQ ID NO 6) were individually bound to two different subsets of microspheres. The microsphere subsets were distinguishable based on unique levels of incorporated orange and red fluorescent dyes. These microsphere subsets were then mixed to form a multiplex set. Each of the complementary probe target pairs represented the internal sequence specific region within the HSV gB gene and the ICC control plasmid.

Upon completion of the PCR reaction described in Example 2, the amplification products are hybridized in a multiplex reaction containing both of the labeled probes and the target microspheres. Fluorescence from the probes is produced and detected by a flow cytometer. (Smith et al., Clinical Chemistry 44:2054–2056 (1998); van Huisden, et al., J. Histochem. 45:315–319 (1997)). If there are inhibitory contaminants within the PCR reaction mixture, then no signal will be seen from either the target sequence or the control plasmid.

The presence of the control plasmid allows the investigator to differentiate a true negative result due to the absence of the target sequence from a negative result due to endogenous inhibition of the PCR reaction. This Example illustrates the utility of this invention, for without the presence of an internal control for inhibition, an investigator would be unable to discern whether the negative result indicated a lack of target or merely internal amplification inhibition.

To illustrate this aspect of the present invention, a serial dilution series of HSV and ICC PCR products, (in equimolar ratios) was aliquoted. Each mixed dilution was detected by both the microtiter capture plate assay described in Example 3 and by FlowMetix flow cytometry. The data are shown in FIG. 4. Duplicate samples were analyzed and averaged. Optical densities for the microtiter plate data are on the x-axis while data from FlowMetrix is on the y-axis. The ICC amplicon data is shown in FIG. 4A. HSV amplicon detection data are in FIG. 4B. These results show a high degree of correlation between the two detection methods.

Use of the ICC for amplification assay calibration and quantification

In another embodiment of the present invention, the ICC may be used as a means to calibrate or quantify the product of an amplification reaction (signal or target). For example, the addition of a known quantity of the ICC to an amplification reaction would permit an investigator to quantitate the amount of target sequence produced against the amount of ICC product produced. The comparison would be especially meaningful since both products are produced within the experimental sample tube of the amplification reaction.

Quantification of a PCR Target Product by Comparison with an ICC Standard

This Example provides a method to quantify the amount of target PCR sequence produced during an amplification assay. The comparison is made possible by knowing the starting concentration of ICC and calculation of the PCR product over a known amplification cycle profile. The ICC is constructed as discussed above. A number of experimental reactions may be amplified containing a number of different ICC starting concentrations. The ICC products may be used as a standard curve with which to predict the amount of starting target sequence. As in the previous examples, the ICC and target templates are present in the same experimental tube. The ICC template and primers may also be run in a separate reaction tube to compare ICC product formation in the presence and absence of target sample.

The PCR reaction is run as described in Examples 1 and 2. The products of that reaction are analyzed as described in Example 3. ICC products produced in the experimental and control tubes are compared and quantified. The amount of product produced by the ICC amplifications is used to construct a standard curve. The amount of target sequence product in the experimental wells is then compared to the amount of ICC product produced. By comparing the amount of product produced from the target sequence with that of the ICC standards, the starting concentration of target sequences is determined.

EXAMPLE 6

In this Example, a PCR reaction including a known quantity of the ICC is run as described in Examples 1 and 2. A variety of methods are known by one skilled in the art for the quantification of plasmid DNA as well as PCR production quantification (e.g., absorbance at 260 nm). The amount of target PCR product can be quantified by comparison to the amount of ICC PCR product produced from a known amount of ICC added to the target amplification reaction.

The internal control plasmid may also be used to perform calibration of inhibitory factors found in patient samples. An internal control for branched oligonucleotide signal amplification An embodiment of the present invention consists of a control sequence wherein the entire internal sequence is reversed. In this configuration, the present invention may be used as an internal control for a branched oligonucleotide signal amplification assay. The branched oligonucleotide signal amplification assay uses a series of probes to bind and amplify a target sequence. For example, human immunodeficiency virus type (HIV-1) RNA was detected and quantified using a branched DNA signal amplification by Pachl et al. (See Pachl et al., "Rapid and Precise Quantification of HIV-1 RNA in Plasma Using a Branched DNA Signal Amplification Assay," Journal of Acquired Immune Deficiency Syndromes and Human Retrovirology, 8: 446–454 (1995); herein incorporated by reference).

In the branched DNA assay (bDNA), the target is bound to a well of a microtiter plate by oligonucleotide probes that bind to and capture the target sequence. After binding, the bound target-capture probe complexes are exposed to another target-capture probe that is also capable of binding a branched DNA molecule as well as the target molecule. An enzyme labeled branched DNA probe is then added to the mixture and exposed to the substrate of the enzyme label. The signal obtained from this enzymatic reaction can be used to quantify the amount of target originally captured by the assay.

The present invention provides a method to control for internal inhibition of the bDNA assay. By using an internal control composed of an inverted sequence of the target molecule, inhibition of primer binding can be controlled. In one embodiment, an inverted control plasmid is constructed and the RNA produced from this plasmid is introduced along with the target sample into the microtitre well. Unlike in the previous embodiments, the same capture probes would not be used for both the control and the target sequences. However, due to the similarity of the sequences, the make up and binding of the control probes to the control sequences would accurately reflect the binding that occurs on the target molecule.

In a manner similar to the PCR example discussed above, the presence of an internal control of inhibition would permit an investigator to more accurately arrive at result indicating a negative or positive result.

EXAMPLE 7

Blood is obtained by routine phlebotomy techniques and tested for the presence of HIV-1 RNA using a branched DNA signal amplification assay. Heparin containing blood collection tubes should not be used as the presence of heparin appears to negatively effect the concentration HIV-1 RNA in the plasma. (See Pachl et al.). Plasma is obtained from the blood samples using centrifugation at 800 g for 10 minutes. The plasma is stored at less that −70° C.

Plasma specimens are treated by the addition of 50 µl of a 0.1% red polystyrene 0.5 µm bead suspension (Bangs Laboratories, Carmel, Ind.) in 10 mM Tris-HCl pH 8.0, 1 mM EDTA to each plasma containing tube. The samples are centrifuged for 1 hour at 23,500 g at 2–8° C. The supernatant is then removed and the viral pellets are extracted for use in the branched DNA assay.

The virus pellets are extracted using 220 µl of Specimen Working Reagent [400 mM LiCl, 100 mM HEPES pH 7.5, 8 mM EDTA, 1% lithium lauryl sulfate, 12 µg/ml sonicated salmon sperm DNA, 0.04% Na azide, 0.04% Proclin 200 (Supelco, Bellefonte, Pa., U.S.A.), 2.2 mg/ml proteinase K, 0.375 pmole/ml of each HIV-1 target probe or control probe to mediate capture, 1.25 pmole/ml of each HIV-1 or control probe to bind amplifier]. The ICC control plasmid may be added to the sample virus pellet before extract or after the extraction procedure is completed. The ICC and the control primers may be kept separated from the target sample and used in a separate well of the assay plate discussed below.

The mixture of virus pellet is then vortexed, incubated at 53° C. for 20 minutes to extract the viral RNA, vortexed again, and centrifuged at 23,500 g for 15 minutes to clarify the pellet extract. The clarified extract (200 µl) is then added to the assay wells of a 96-well assay plate which is coated with either HIV-1 capture probes or control probes or a mixture of the two. Other standards in addition to the ICC inhibition control may also be used.

The assay plate is then incubated at 53° C. to permit the binding of the target or ICC control molecules to their respective probes. The wells are then allowed to cool to room temperature for 10 minutes and are then washed twice with Wash A, a standard saline citrate (SSC)-0.1% SDS buffer. An amplification buffer containing 2.0 pmole/ml bDNA amplifier in Amplifier Diluent (50% horse serum, 1.3% SDS, 6mM Tris-HCl pH 8.0, 5× SSC), is added along with 0.5 mg/ml proteinase K and is incubated at 65° C. for 2 hours. This incubation is followed by the addition of 1 mM phenylmethylsulfonyl fluoride (PMSF) to inactivate the proteinase K, and 0.05% each Na azide and Proclin 300.

The wells are then sealed and incubated at 53° C. for 30 minutes in order to hybridize the bDNA amplifier molecules to the target-probe or control-probe complexes on the microwell surface. The wells were subsequently cooled and washed as above, followed by the addition of 50 µl of HIV Label Working Reagent (4 pmole/ml alkaline phosphatase-labeled probe in Amplifier Diluent). The wells are then sealed and incubated at 53° C. for 15 minutes to hybridize the alkaline phosphatase probe to the immobilized bDNA amplifier molecules. The wells are then cooled as above and washed twice with Wash A followed by three washes with Wash B (0.1× SSC). A 50 µl volume of chemiluminescent substrate, an enzyme triggerable dioxetane substrate for alkaline phosphate (Lumiphos 530, Lumigen, Detroit, Mich., U.S.A.) is added to each well and incubated at 37° C. for 30 minutes. Light emission is then measured in a luminometer.

An internal control for RNA amplification reactions (RT-PCR)

In another embodiment, the positive control is a RNA molecule. When an RNA molecule is the target of a signal amplification assay, a RNA molecule should be used as a positive inhibition control. RT-PCR refers to the use of reverse transcriptase in the PCR reaction. Since RNA molecules are more labile to degradation than double stranded DNA, it is appropriate to control for degradation using the same type of nucleic acid. In a preferred embodiment, a PCR based RNA amplification assay is used.

EXAMPLE 8

The following protocol is based on Current Protocols in Molecule Biology Volume 2, Chapter 15.4 (1995), which is incorporated herein by reference.

A target RNA molecule is used as a template in the PCR reaction. A sample of RNA is obtained through standard methods known in the art. The RNA used in the signal amplification reaction may be poly(A)+ RNA, or total RNA may be used. Alternatively cytoplasmic RNA may be used. The type of RNA used in the reaction will determine the type of control RNA used. The control RNA may also be added directly to the sample containing the target RNA for testing purposes.

A solution is prepared of 2 μg of RNA, 25 ng (3 pmol) cDNA primer, and sufficient $H_2O$ to bring the volume to 90 μl. After mixing, 10 μl of 3 M sodium acetate, pH 5.5 and 200 μl of 100% are added. This solution is mixed and allowed to precipitate overnight at −20° C. or for 15 minutes at −70° C. The sample is then centrifuged for 15 minutes at high speed at 4° C. The resulting pellet is saved and the supernatant is discarded. The pellet is washed with 70% ethanol and centrifuged for 5 minutes at high speed, room temperature. The supernatant is discarded. The pellet is dried briefly in a desiccator.

The following ingredients are added to the RNA pellet: 12 μl $H_2O$, 4 μl 400 mM Tris-HCl, pH 8.3, and 4 μl 400 mM KCl. The solution is heated to 90° C. and then cooled slowly to 67° C. The sample is briefly microfuged to collect any condensate that may have formed and incubated for 3 hours at 52° C. Again, the sample is briefly microfuged to collect any condensate.

A complementary or cDNA molecule is synthesized in the next step. Twenty-nine microliters of reverse transcriptase buffer (50 mM Tris-HCl, pH 8.2, 5 mM MgCl2, 5 mM DTT, 50 mM KCl, 50 μg/ml BSA) and 0.5 μl (16U) avian myeloblastosis virus (AMV) reverse transcriptase are combined. These reagents are mixed and incubated for 1 hour at 42° C. One hundred fifty microliters of 10 mM Tris-HCl/10 mM EDTA, pH 7.5 are combined and the solution is mixed again. The solution is phenol extracted with 200 μl buffered phenol and vortexed. The sample is microcentrifuged for 5 minutes at high speed, and the aqueous phase is saved. The mixture is chloroform extracted with a solution of 24:1 chloroform:isoamyl alcohol and vortexed. The sample is microcentrifuged for 5 minutes at high speed, and the aqueous phase is retained. The solution is precipitated with 20 μl of 2M sodium acetate, pH 5.5, and 500 μl of 100% ethanol overnight at −20° C. or for 15 minutes at −70° C. The sample is microfuged for 15 minutes at high speed for 4° C. and the supernatant is discarded. The pellet is briefly dried and resuspended in 40 μl of $H_2O$. This material is the template in the PCR reaction.

Following precipitation of the cDNA, the target and control molecules are amplified using PCR. To a 5 μl sample of cDNA 5 μl of each amplification primer (20 μM each) is added. To that 4 μl of 5 mM dNTP mix (see PCR protocol above), 10 μl of 10× PCR amplification buffer and 70.5 μl of $H_2O$ is added and the reaction mixture is heated at 94° C. The sample is microcentrifuged and 2.5 U of Taq DNA polymerase is added to the reaction mixture. The solution is overlaid with 100 μl of mineral oil before the reaction is run. Forty or more cycles in an automated thermocycler are performed to amplify the target molecules.

The reaction products are then assayed for the presence or absence of control sequence as discussed in Example 3 or 5.

Enantiomeric and reversed amino acid sequences used for internal controls

Another aspect of the present invention contemplates the use of reversed amino acid sequences and enantiomeric sequence as controls for immunological assays. Enantiomers are compounds that have the ability to rotate the plane of plane-polarized light as it passes through a solution. Such compounds are asymmetric so that they can exist in two different structural forms (D and L forms). Each of the structural forms exist as mirror images of each other and has the capability of rotating light in a particular direction. Proteins are naturally occurring polymers of L-amino acids. Synthetic enantiomers of naturally occurring proteins and smaller peptide sequences can be readily chemically synthesized using D-forms of amino acids. These peptides can then be used as controls for immunoassays.

An important reagent in many immunoassays is antibodies. Monoclonal or polyclonal antibodies are raised to a specific amino acid sequence within the protein of interest. The techniques to raise antibodies are well known in the art. For example, see Antibodies: A Laboratory Manual, (Harlow and Lane, Eds.), Cold Spring Harbor Laboratory (1988). The amino acid sequence of a target protein, consisting of naturally occurring L-amino acids, is determined using standard techniques known in the art. An enantiomeric sequence, identical to the native epitope, only using D-amino acids is synthesized and used to raise antibodies.

Chemical methods of peptide synthesis are well known in the art. The use of tertiary-butyloxycarbonyl blocking groups (t-Boc chemistry) or fluoromethoxy carbonyl blocking groups (Fmoc) are two such methodologies. Once individual D-amino acids are synthesized and fitted with blocking groups, a short D-peptide is synthesized. In one embodiment solid-phase synthesis is used. Following decoupling from the synthetic resin the D-peptides are purified using high performance liquid chromatography (HPLC). The conditions for such purification depend on the amino acids used to form the D-peptides. The peptide sequences are confirmed through amino acid sequencing techniques that are also well known in the art.

Following the synthesis of the D-peptides, an antibody would be raised against it. Monoclonal antibody production is well known in the art. Briefly, a target animal, preferably a mouse, would be immunized with the D-peptides. After an appropriate number of booster immunizations, the spleen of the immunized animal is harvested and used to create hybridomas using techniques well known in the field. Following hybridoma generation, individual colonies are screened for antibody production. Those colonies that produce active antibody can be expanded to produce large quantities of the monoclonal antibody. (See Antibodies, A Laboratory Manual, Chapter 7, eds. Ed Harlow & David Lane, Cold Spring Harbor Laboratory (1988), herein incorporated by reference).

In a preferred embodiment, the D-peptides and the monoclonal antibodies generated against them are used as a control for inhibition. Control D-peptides that are enantiomers to a known target antigen are added to a sample in a detectable quantity. In a preferred embodiment the control antigen is added in a range from 1 to 100 ng/well. Antibodies specific for both the target epitope and the control D-peptides are added to the mixture. In a preferred embodiment the two classes of antibodies are bound to two different fluorescent bead populations so that the binding of control and target antibodies may be determined. As with the other embodiments of this invention, the absence of binding of the control antibody to the control D-peptides would indicate inhibition of the assay.

Immunoassays are well known in the art and involve the detection an antibody or an antigen. For example, a well-known form of immunoassay is the enzyme linked immunosorbent assay or ELISA assay. In this immunoassay an antigen is bound to the bottom of an assay plate and exposed to a sample of plasma that contains antibodies. The assay plate is then washed and then exposed to an anti-antibody antibody coupled to some signal-producing molecule, like an enzyme. The assay plate is then screened for the presence of a signal. The presence of a signal indicates antibody binding and therefore the presence of antigen. Often, the level of signal produced can be used to determine the quantity of antigen bound to the bottom of the well.

Assays such as the ELISA are extremely useful for screening samples for the presence of particular proteins. For example, if a person has been exposed to HIV then it is likely that that person will carry antibodies specific for certain HIV proteins. If that person wishes to donate blood, then their blood may be screened for antibodies against HIV that would suggest that the donated blood was contaminated with HIV. On the other hand, a negative result could be improperly interpreted as the absence of HIV exposure if that negative result was due to inhibition of the assay. If some molecule was inhibiting the assay mechanism, an investigator could incorrectly conclude that the sample tested was free of HIV antibodies. An internal control for inhibition would permit investigators who monitor the blood supply to accurately differentiate a true positive from a false positive test result.

EXAMPLE 9

A blood sample is taken using standard techniques known in the art and tested for the presence of the HIV protein, gp24 protein. Antibodies to an epitope of the gp24 protein as well as its enantiomer are generated as discussed above. The blood sample is processed for use in an ELISA assay.

An ELISA assay is performed to test for the presence or absence of the gp24 protein according to protocols well known in the art. A standard microtiter plate containing positive and negative controls as well as experimental wells is assembled. To control for inhibition, a detectable amount of gp24 enantiomer epitope is included in the experimental wells of the assay. In one experimental well, an antibody specific for the gp24 epitope is used in the assay. In another experimental well, an antibody specific for the gp24 enantiomer epitope is used. Reagents that detect the presence of anti-gp24 or gp24 enantiomer antibodies are then added to the assay. The results from the assay are then analyzed.

The presence of a negative response from the anti-gp24 containing wells of the assay suggests that the tested blood lacks detectable gp24. Nevertheless, the lack of signal from this well may instead result from inhibition of binding by the anti-gp24 antibody. To determine whether inhibition is present in the experimental well, the results from the experimental well assayed with the anti-gp24 enantiomer antibody are examined. If a positive signal is present in this well, then there was no inhibition, since the anti-gp24 enantiomer antibody reacted with its target epitope. On the other hand, if there is no signal from the anti-gp24 enantiomer antibody containing wells, then inhibition of the ELISA assay may be present and the investigator may not conclude that the assayed blood sample is free from gp24.

An internal control for Nucleic Acid Amplification Based Amplification (NASBA) and Transcription Mediated Amplification (TMA)

In another aspect of the present invention, the ICC may be used as an internal inhibition control for a NASBA target amplification assay. The NASBA and TMA technologies are isothermal nucleic acid amplification assays that are virtually identical in principle and practice. These isothermal nucleic acid amplification assays use oligonucleotide probes, an RNA dependent polymerase and a reverse transcriptase to amplify a target sequence. An isothermal nucleic acid amplification assay, unlike PCR, is an isothermal amplification method, thus it does not cycle between high and low temperatures to facilitate target amplification. For example, the amplification of human immunodeficiency virus type (HIV-1) RNA was described using a NASBA signal amplification (See Kievits et al., "NASBA TM isothermal enzymatic in vitro nucleic acid amplification optimized for the diagnosis of HIV-1 infection," Journal of Virological Methods, 35: 273–286 (1991); herein incorporated by reference).

In a NASBA assay, for example, the target RNA molecule is placed into solution with oligonucleotide primers and two polymerases. The temperature of the sample is raised to prepare the target molecules for amplification. The temperature is then lowered to permit the primer bind to the template. After binding the target, a DNA molecule complementary to the target sequence is synthesized using a reverse transcriptase, such as the AMV-reverse transcriptase. Subsequent to this synthesis, the RNA-DNA hybrid molecule is digested with RNase H, removing the RNA strand. A complementary strand to the single stranded DNA target sequence is synthesized through another round of DNA polymerization using a reverse transcriptase enzyme.

Following the creation of this double stranded DNA molecule, single stranded RNA is synthesized from the double stranded DNA template with T7 RNA polymerase. This step amplifies the original target sequence 100 to 1000-fold. Simultaneously, new double stranded DNA templates are being synthesized from the replicated single stranded RNA templates produced in the first round of amplification. From this series of reactions, the target sequence is amplified. The products of this reaction can be assayed to determine the presence or absence of a target molecule. Quantitation of the product created by the reaction is possible using the methods described herein. Also, with the inclusion of the ICC sequence of the present invention, a clinician using NASBA to assay for the presence or absence of a target molecule could accurately determine if inhibition of the reaction occurred, resulting in a possibly false negative response.

EXAMPLE 10

Blood is obtained by routine phlebotomy techniques and tested for the presence of HIV-1 RNA using a NASBA signal amplification assay. A nucleic acid sample is isolated from the plasma using generally known methods. (See Boom et al., "A rapid and simple method for purification of nucleic acids," J. Clin. Microbiol. 28, 495–503 (1990); herein incorporated by reference). The isolated nucleic acid is resuspended in water and stored at −70° C.

Two microliters of isolated nucleic acid solution are mixed with 23 µl of a reaction mixture containing (at a final concentration in a 25 µl reaction mixture): 40 mM Tris, pH 8.5, 12 mM MgCl$_2$, 42 mM KCl, 15% v/v DMSO, 1 mM each of dNTP, 2 mM each NTP, 0.2 µM Primer 1, 0.2 µM Primer 2, 2 µl of ICC internal control RNA in a known quantity at a sufficiently high concentration to provide a signal from the NASBA assay.

The sample is incubated at 65° C. for 5 minutes, destabilizing any secondary structures in the nucleic acid target. The mixture is cooled to 41° C. and the primers are thus annealed to the template. The amplification reaction is started by adding 2 µl enzyme mixture (0.1 µg/µL BSA, 0.1 units RNase H, 40 units T7 RNA polymerase and 8 units AMV-reverse transcriptase). The reaction mixture is incubated at 41° C. for 90 minutes. The reaction mixture is then assayed for target and control signal amplification. The absence of a signal from the ICC control signal indicates inhibition of the signal amplification reaction.

EXAMPLE 11

Transcription-Mediated Amplification (TMA) Assay

A blood sample is tested for the presence of the HSV gB gene transcript according to the TMA protocol described in Stary, A., et al., "Performance of transcription-mediated amplification and ligase chain reaction assays for detection of chlamydial infection in urogenital samples obtained by invasive and noninvasive methods." J Clin Microbiol. 36(9):2666–70 (1998). A negative response from an experimental sample containing the ICC control indicates the presence of inhibtion.

Molecular Beacons

The term molecular beacons relates to an assay system that utilizes probes that fluoresce upon hybridization with a target sequence. Molecular beacons are discussed in Tyagi & Kramer, "Molecular Beacons: Probes that Fluoresce upon Hybridization," Nature Biotechnology, 14:303–308 (1996) and in Giesenfor, et al., "Molecular beacons: a new approach for semiautomated mutation analysis," Clinical Chemistry 44:482–486 (1998). The principle of this assay system involves a probe that consists of a stem-and-loop structure. The loop portion of the molecule is a probe sequence complementary to a predetermined target sequence. The stem is formed by annealing on either side of the probe sequence two complementary arm sequences that are unrelated to the target sequence. A fluorophore is attached to the end of one arm and a quenching moiety is attached to the end of the other arm. The stem keeps these two moieties in close proximity to each other and quenches the signal from the fluorophore. Once the molecular beacon binds to its target, the fluorophore is separated from the quencher, permitting a signal to be generated from the probe. Thus, the probe undergoes a spontaneous conformational change that forces the arm sequences apart, thereby moving the fluorophore and the quencher away from each other and resulting in the generation of fluorescence.

As with any assay system, the production of a signal provides a basis to conclude that the target sequence is present in the experimental sample. The converse does not necessarily hold, however, since the absence of a signal in a hybridization assay may result from amplification inhibition rather than the absence of target from the assayed sample. The present invention may be used as an internal inhibition control to determine whether the absence of a signal is a legitimate negative result or merely a result of inhibition.

EXAMPLE 12

A blood sample is prepared from an individual to be screened for the presence of HSV gB. The blood sample is obtained and prepared by methods well known in the art. Molecular probes specific for the HSV gB (SEQ. I.D. NO. 7) and ICC (SEQ. I.D. NO. 8) sequences are constructed according to the method of Tyagi and Kramer.

One hundred and fifty µl of a 170 nM solution of molecular beacon probe SEQ ID NO 7 and 8 are separately dissolved in 100 mM Tris-HCl (pH 8) containing 1 mM MgCl$_2$ that is maintained at 25° C. The fluorescence of each probe solution is monitored at 490 nm with time in an LS-5B spectrofluorometer (Perkin Elmer), using 1 cm path length QS curvettes (Hellma) whose temperature is controlled by a circulating water bath. There is no change in fluorescence with time, so a sample containing 5-fold molar excess of target sequence and ICC are added to curvettes containing the probes. The level of fluorescence emitted is recorded.

The temperature of the sample is gradually increased to denature the probe and promote hybridization from 25° C. to 75° C. at a rate of 2° C./minute. As the temperature increases, the amount of fluorescence detected from the samples containing the ICC and ICC specific probe increases. In the experimental reaction mix, no signal is detected from the HSV gB probe. Since there is signal from the ICC probe, there is no inhibition of this experimental preparation.

EXAMPLE 13

Molecular Beacons and Real-Time PCR Analysis

A blood sample is prepared from an individual to be screened for the presence of HSV gB using real-time PCR. This procedure entails monitoring the generation of fluorescence during the various PCR cycles using an ABI 7700 Sequence Detector (Perkin-Elmer/Applied BioSystems). The blood sample is obtained and prepared for use in PCR by methods well known in the art. Molecular beacons specific for the HSV gB (SEQ. I.D. NO. 7) and ICC (SEQ. I.D. NO. 8) sequences are constructed according to the method of Tyagi and Kramer. The molecular beacons are labeled with different fluorescent probes to emit different signals when bound. Alternatively, the beacons may be labeled with the same probe and to added to different reaction mixtures to monitor target sequence synthesis and control sequence synthesis separately.

The PCR samples are assembled as discussed in the Examples above. PCR primers, SEQ ID NOS 3 and 4 are used to amplify the target and control sequences. The PCR reaction buffer is as described above with the addition of a fluorescent dye at 60 nmol final concentration (ROX, Perkin-Elmer). The molecular beacons are added directly to the PCR mix. To the individual PCR reactions are added blood samples or controls. To each of these is added the PCR mix as well as a sample of ICC. The PCR tubes containing the individual reactions are then subjected to thermocycling.

At 95° C., the molecular beacons are denatured and have a random coil structure, allowing full fluorescence. During the decrease of the temperature in the PCR cycle, the formation of hairpins occurs, which causes a drop in fluorescence. In samples containing lacking the HSV target sequence the molecular beacons fails to bind to their complementary sequences and there is no increase in the fluorescence detected. However, in those experimental reactions containing the molecular beacon specific for the control sequence, molecular beacon binding to their complementary sequences does occur and fluorescence increases.

From these results the investigator may reasonably conclude that there is no signal inhibition and the negative result observed reflects an absence of target sequence in the experimental PCR reaction.

We claim:

1. A method for detecting signal amplification inhibition in an assay comprising:

co-amplifying a target sequence and an internal control cassette, wherein the entire internal control cassette is in reverse orientation relative to the target sequence, whereby co-amplification products are produced; and assaying the co-amplification products for the presence of the internal control casette wherein the absence of the internal control cassette as an amplification product is an indication of signal amplification inhibition.

2. The method of claim 1, wherein the assay is selected from the group consisting of PCR, nucleic acid sequence based on amplification assays (NASBA), and transcription mediated amplification (TMA).

3. The method of claim 1, wherein the target sequence comprises DNA or RNA.

4. The method of claim 3, wherein the target sequence is a nucleic acid sequence from a virus selected from the group consisting of HSV, HIV, HCV, CMV, and HPV.

5. The method of claim 4, wherein the target sequence comprises the nucleic acid sequence of SEQ. ID. NO. 1.

6. The method of claim 5, wherein the internal control cassette comprises the nucelic acid sequence of SEQ. ID. NO. 2.

7. The method of claim 1, wherein the step of assaying products is a primer binding assay comprising the steps of:

determining the extent of product binding to a capture probe specific for the internal control casette product.

8. The method of claim 7, wherein the capture probe consists of the nucleic acid of SEQ ID NO. 6.

9. The method of claim 1, further comprising contacting one or more hybridization probes with the target sequence, the internal control cassette or both.

10. The method of claim 9, wherein the assay is a molecular beacon assay.

11. The method of claim 9, wherein the hybridization probe comprises the nucleic acid sequence of SEQ. ID. NO. 8.

12. The method of claim 1, wherein the target sequence and the internal control cassette are in the same assay environment.

13. The methof of claim 12, wherein the target sequence and the internal control casette are co-amplified in the same well.

* * * * *

UNITED STATES PATENT AND TRADEMARK OFFICE
CERTIFICATE OF CORRECTION

PATENT NO. : 6,395,470 B2  Page 1 of 1
DATED : May 28, 2002
INVENTOR(S) : Cindy R. WalkerPeach et al.

It is certified that error appears in the above-identified patent and that said Letters Patent is hereby corrected as shown below:

Column 23,
Line 39, "in reverse" should read -- in a reverse --
Lines 42 and 43, "casette" should read -- cassette --
Line 57, "nucelic" should read -- nucleic --

Column 24,
Line 54, "methof" should read -- method of --

Signed and Sealed this

Tenth Day of June, 2003

JAMES E. ROGAN
*Director of the United States Patent and Trademark Office*